United States Patent
Dabrowiak et al.

(10) Patent No.: US 9,801,756 B2
(45) Date of Patent: Oct. 31, 2017

(54) INTRAVASCULAR HEAT EXCHANGE CATHETER AND SYSTEM WITH RFID COUPLING

(71) Applicant: Zoll Circulation, Inc., Sunnyvale, CA (US)

(72) Inventors: Jeremy T. Dabrowiak, Redwood City, CA (US); James Palazzolo, Sunnyvale, CA (US); Richard A. Helkowski, Redwood City, CA (US)

(73) Assignee: ZOLL CIRCULATION, INC., San Jose, CA (US)

( * ) Notice: Subject to any disclaimer, the term of this patent is extended or adjusted under 35 U.S.C. 154(b) by 495 days.

(21) Appl. No.: 13/658,964

(22) Filed: Oct. 24, 2012

(65) Prior Publication Data

US 2014/0094881 A1    Apr. 3, 2014

Related U.S. Application Data

(60) Provisional application No. 61/707,159, filed on Sep. 28, 2012.

(51) Int. Cl.
*A61F 7/12* (2006.01)
*A61B 90/98* (2016.01)

(52) U.S. Cl.
CPC .............. *A61F 7/12* (2013.01); *A61B 90/98* (2016.02); *A61F 2007/126* (2013.01)

(58) Field of Classification Search
CPC . A61F 7/12; A61F 2007/126; A61B 2019/448

(Continued)

(56) References Cited

U.S. PATENT DOCUMENTS 1,459,112 A    6/1923   Mehl
1,857,031 A    5/1932   Schaffer
(Continued)

FOREIGN PATENT DOCUMENTS

DE     19531935    2/1997
GB     2040169     8/1980
(Continued)

OTHER PUBLICATIONS

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

(Continued)

*Primary Examiner* — Thomas Giuliani
(74) *Attorney, Agent, or Firm* — John L. Rogitz

(57) ABSTRACT

A system includes a heat exchange catheter line assembly configured to convey working fluid circulating to and from at least one heat exchange element on an intravascular heat exchange catheter. The system also includes a heat exchange system that itself includes a processor and is configured for fluidly communicating with the heat exchange catheter line assembly to exchange heat with the working fluid. A near field communication (NFC) member associated with the heat exchange system and an NFC element associated with the heat exchange catheter line assembly are also included. The NFC member is configured to provide the processor with a signal representative of whether the NFC member detects the NFC element.

20 Claims, 1 Drawing Sheet

(58) Field of Classification Search
USPC .................................................. 607/105, 113
See application file for complete search history.

(56) References Cited

U.S. PATENT DOCUMENTS

| | | |
|---|---|---|
| 2,663,030 A | 12/1953 | Dahlberg |
| 2,673,987 A | 4/1954 | Upshaw et al. |
| 3,225,191 A | 12/1965 | Calhoun |
| 3,369,549 A | 2/1968 | Armao |
| 3,425,419 A | 2/1969 | Actis Dato |
| 3,504,674 A | 4/1970 | Swenson |
| 3,726,269 A | 4/1973 | Webster, Jr. |
| 3,744,555 A | 7/1973 | Fletcher et al. |
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 6,019,783 A * | 2/2000 | Philips et al. ................. 607/105 |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | DiMagno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaivolo et al. |
| 6,635,076 B1 | 10/2003 | Ginsburg |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Wemeth |
| 6,719,779 B2 | 4/2004 | Daoud |
| 6,726,653 B2 | 4/2004 | Noda et al. |
| 6,733,495 B1 | 5/2004 | Bek et al. |
| 6,740,109 B2 | 5/2004 | Dobak, III |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,510,569 B2 | 3/2009 | Dae et al. |
| 7,666,215 B2 | 2/2010 | Callister et al. |
| 7,822,485 B2 | 10/2010 | Collins |
| 7,846,193 B2 | 12/2010 | Dae et al. |
| 7,857,781 B2 | 12/2010 | Noda et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0145525 A1 | 10/2002 | Friedman et al. |
| 2002/0183692 A1 | 12/2002 | Callister |
| 2002/0198579 A1 | 12/2002 | Khanna |
| 2003/0236496 A1 | 12/2003 | Samson et al. |
| 2004/0089058 A1 | 5/2004 | De Hann et al. |
| 2004/0102825 A1 | 5/2004 | Daoud |
| 2004/0171935 A1* | 9/2004 | Van Creveld ............ A61B 8/00 600/437 |
| 2004/0210231 A1 | 10/2004 | Boucher et al. |
| 2005/0156744 A1 | 7/2005 | Pires |

(56) References Cited

U.S. PATENT DOCUMENTS

| | | | |
|---|---|---|---|
| 2007/0007640 A1 | 1/2007 | Harnden et al. | |
| 2007/0076401 A1 | 4/2007 | Carrez et al. | |
| 2007/0093710 A1* | 4/2007 | Maschke | 600/407 |
| 2009/0065565 A1* | 3/2009 | Cao | 235/375 |
| 2010/0204765 A1 | 8/2010 | Hall et al. | |
| 2012/0095536 A1 | 4/2012 | Machold et al. | |

FOREIGN PATENT DOCUMENTS

| | | |
|---|---|---|
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| JP | 2003508150 | 3/2003 |
| JP | 2008154751 | 7/2008 |
| JP | 2011505929 | 3/2011 |
| JP | 2011182849 | 9/2011 |
| WO | 9001682 | 2/1990 |
| WO | 9304727 | 3/1993 |
| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 0010494 | 3/2000 |
| WO | 0113809 | 3/2001 |
| WO | 0164146 | 9/2001 |
| WO | 0176517 | 10/2001 |
| WO | 0183001 | 11/2001 |
| WO | 2009056640 | 5/2009 |

OTHER PUBLICATIONS

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

* cited by examiner

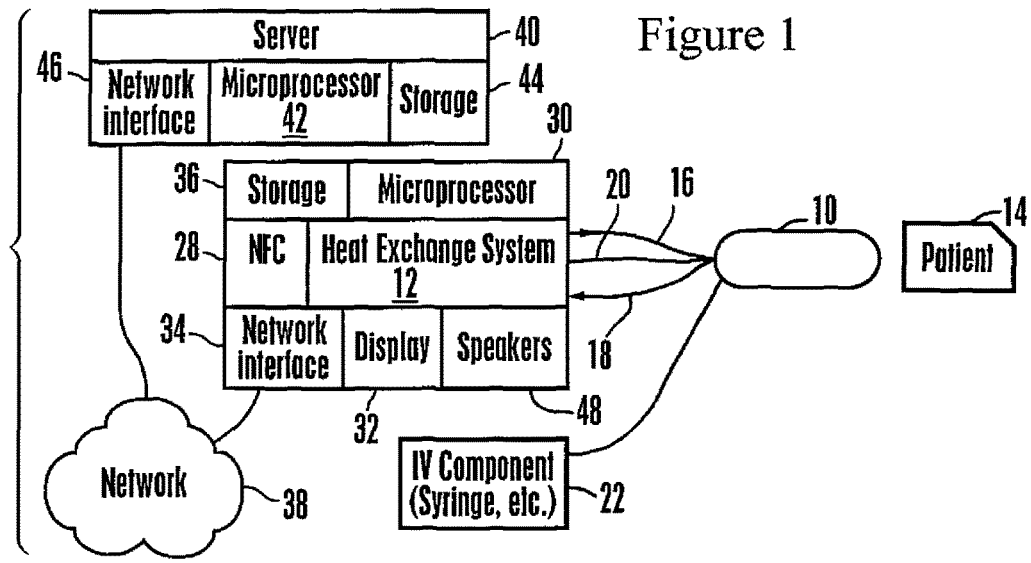
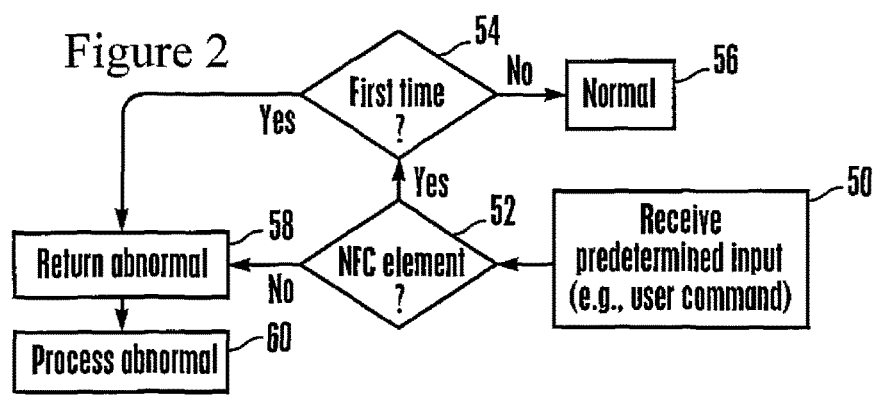

US 9,801,756 B2

INTRAVASCULAR HEAT EXCHANGE CATHETER AND SYSTEM WITH RFID COUPLING

I. FIELD OF THE INVENTION

The present application relates generally to patient temperature control systems.

II. BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, skin graft surgery, and the like, it might be desirable to rewarm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight, non-helical heat exchange elements), U.S. Pat. Nos. 6,126,684, 6,299,599, 6,368,304, and 6,338,727 (catheters with multiple heat exchange balloons), U.S. Pat. Nos. 6,146,411, 6,019,783, 6,581,403, 7,287,398, and 5,837,003 (heat exchange systems for catheter), U.S. Pat. No. 7,857,781 (various heat exchange catheters).

SUMMARY OF THE INVENTION

Accordingly, a system includes a heat exchange catheter line assembly configured to convey working fluid circulating to and from at least one heat exchange element on an intravascular heat exchange catheter. The system also includes a heat exchange system that itself includes a processor and is configured for fluidly communicating with the heat exchange catheter line assembly to exchange heat with the working fluid. A near field communication (NFC) member associated with the heat exchange system and an NFC element associated with the heat exchange catheter line assembly are also included. The NFC member is configured to provide the processor with a signal representative of whether the NFC member detects the NFC element.

In some embodiments, the heat exchange catheter line assembly may be established by the intravascular heat exchange catheter, a tubing set configured to engage the intravascular heat exchange catheter, or a combination of both. Also in some embodiments, the NFC member may be a radiofrequency identification (RFID) reader and the NFC element may be an RFID tag.

Furthermore, if desired the processor included on the heat exchange system may be configured under at least one predetermined condition to generate a warning signal to activate a visual and/or audible warning to a human operator that an approved heat exchange catheter line assembly is not present responsive to a signal from the NFC member that the NFC member does not detect the NFC element. Also if desired, the processor may be configured under at least one predetermined condition to prevent heat exchange operation of the heat exchange system responsive to a signal from the NFC member that the NFC member does not detect the NFC element.

In another aspect, a method includes configuring an NFC element for a heat exchange catheter line assembly to communicate with an NFC reader associated with a heat exchange system to cause the NFC reader to determine that the heat exchange catheter line assembly is an assembly approved for use with the heat exchange system based on the communication. The method also includes providing the NFC element to an operator of the heat exchange system for use with the heat exchange system. The NFC element may be provided by itself or with the heat exchange catheter line assembly.

In still another aspect, an apparatus includes a heat exchange catheter line assembly configured to convey working fluid circulating to and from at least one heat exchange element on an intravascular heat exchange catheter, where the assembly is also configured for fluidly communicating with a heat exchange system to exchange heat with the working fluid. The apparatus also includes an NFC element associated with the heat exchange catheter line assembly and configured to communicate with an NFC member, where the NFC member is associated with the heat exchange system. Moreover, the NFC element is configured to communicate with the NFC member to cause the NFC member to provide a processor on the heat exchange system with a signal indicating that the heat exchange catheter line assembly is an assembly authorized for use with the heat exchange system.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a schematic diagram showing an example catheter engaged with an example heat exchange system;

FIG. 2 is a flow chart of example logic according to present principles; and

FIGS. 3-5 are screen shots of example user interfaces (UIs) that may be presented on the display of the heat exchange system according to present principles.

DETAILED DESCRIPTION OF THE PREFERRED EMBODIMENT

Referring initially to FIG. 1, an intravascular temperature management catheter 10 is in fluid communication with a catheter temperature control system 12 is shown. The system 12 includes a processor executing logic that in some non-limiting examples is in accordance with disclosure in the above-referenced system patents to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as, but not limited to, saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., a patient suffering from sub-arachnoid hemorrhage or intracerebral hemorrhage. Thus, the catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

As shown, working fluid such a refrigerant may be circulated between the temperature control system 12 and catheter 10 through supply and return lines 16, 18 that connect to the proximal end of the catheter 10 as shown. Note that as used herein, "proximal" and "distal" in reference to the catheter are relative to the system 12. A patient temperature signal from a catheter-borne temperature sensor may be provided to the system 12 through an electrical line 20 or wirelessly if desired. Alternatively, a patient temperature signal may be provided to the system 12 from a separate esophageal probe or rectal probe or tympanic sensor or bladder probe or other temperature probe that measures the temperature of the patient 14.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc. Thus, note that in accordance with present principles, the supply and return lines 16 and 18, the electrical line 20, and/or the catheter 10 (which may include an NFC element to be shortly described) may comprise a heat exchange catheter line assembly to be used in conjunction with the system 12 to, e.g., cool a patient as set forth above.

Continuing in reference to FIG. 1, the catheter 10 also includes a near field communication (NFC) element 24 that includes an NFC chip 26 that may be, e.g., an RFID tag. The NFC element 24 including the chip 26 may communicate with an NFC member 28 on the system 12 in accordance with the present principles.

Note that the NFC member 28 may be an RFID reader. Thus, the NFC member 28 may be, e.g., an RFID reader able to read electro-magnetic fields from the NFC element 24 and/or communicate with the NFC element 24. Accordingly, the NFC element 24 and NFC member 28 may establish a no-contact system such that the NFC element 24 and NFC member 28 need not necessarily contact each other to communicate and/or exchange information, although it is to be understood that, if desired, the NFC element 24 and NFC member 28 may be configured to require contact to communicate and/or exchange information. The NFC element 24 and NFC 28 may have their own respective power sources, such as, e.g., respective batteries, although it is to be understood that, e.g., the NFC element 24 may not require a separate power source and may use electro-magnetic fields to be powered in accordance with NFC principles.

Furthermore, note that in exemplary embodiments, the communication between the NFC element 24 and NFC member 28 using RFID technology may be bi-directional, though it is to be understood that any other suitable NFC technology may also be used in accordance with present principles. For example, other technologies and/or components that may be used include Bluetooth, WiFi, a wireless LAN technology employing secure communication standards, smart cards, and/or still other wireless security chips, readers, and technologies (e.g., technologies using encryption keys, security algorithms, "secret keys," public and private keys, etc.). However, note that still other identification technologies may be used in addition to, or in lieu of, what is set forth above, such as, e.g., 2D or 3D hologram security technology.

Regardless, it is to be understood that the NFC member 28 is configured to provide a processor 30 on the system 12 with a signal representative of whether the NFC member 28 detects the NFC element 24 and, if so, the NFC member 28 may also provide a signal indicating whether a heat exchange catheter line assembly associated with the NFC element 24 is an authorized assembly. Accordingly, the processor 30 may be configured under at least one predetermined condition such that, e.g., responsive to a signal from the NFC member 28 that the NFC member 28 does not detect the NFC element 24, the processor 30 may generate a warning signal to activate a visual and/or audible warning on a display 32 and/or at least one speaker 48 of the system 12 to notify a human operator that an approved heat exchange catheter line assembly as described above is not present. Note that the display 32 may be any display suitable for displaying information in accordance with present principles, such as, e.g., a digital display, an LCD display, an LED display, etc.

Still other warnings may be generated in accordance with present principles, such as, e.g., a warning indicating that the catheter and/or tubing set (e.g., including the supply and return lines 16 and 18) have been previously used. Furthermore, a warning of prior use of the catheter and/or tubing set may also include a warning that such use is unsanitary and/or may cause harm to the patient 14, violates a use agreement with the manufacturer of the system 12, catheter 14, and/or tubing set (e.g., the supply and return lines 16 an 18), or otherwise violates a licensing agreement.

Another exemplary predetermined condition may be that, responsive to a signal from the NFC member 28 that the NFC member 28 does not detect the NFC element 24, the processor 30 prevents heat exchange operation of the system 12. The processor 30 may also indicate on the display 32 that heat exchange operation of the system 12 has been prevented, if desired.

Still in reference to FIG. 1, also note that the system 12 may include at least one network interface 34 for communication over at least one network 38 such as the Internet, an WAN, an LAN, etc. in accordance with present principles, and may be, e.g., a wired or wireless modem or router, or other appropriate interface such as, e.g., a wireless telephony transceiver. Also included on the system 12 is at least one tangible computer readable storage medium 36 such as disk-based or solid state storage, as well at least one speaker 48 as mentioned above for outputting sounds such as the audio alerts, warnings, notifications, etc., described herein.

Thus, it is to be understood that the network interface 34, under control of the processor 30, allows for communication by the system 12 with a server 40 that may be, e.g., an Internet server. Note that the server includes at least one processor 42, at least one tangible computer readable storage medium 44 such as disk-based or solid state storage, and at least one network interface 46 for communication over the network 38 in accordance with present principles and may be, e.g., a wired or wireless modem or router, or other appropriate interface such as, e.g., a wireless telephony transceiver. It may now be appreciated that the network interface 46, under control of the processor 42, allows for communication with the system 12 through the respective interfaces 34 and 46.

Before moving on to the logic shown in FIG. 2, also note that the processors 30 and 42 are capable of executing all or part of the logic discussed below to undertake present principles, although in exemplary embodiments the logic of FIG. 2 may be executed by a processor on a temperature control system, such as the processor 30 described above. Moreover, software code implementing present logic executable by, e.g., the processors 30 and 42 may be stored on one or more of the mediums shown (the computer readable storage mediums 36 and 44) to undertake present principles, it being understood that the mediums 36 and 44 are accessible at least to the processors 30 and 42, respectively. For completeness, further note that, e.g., the processor 30 communicates with the NFC member 28 to send and receive signals therewith, and that the display 32 presents information in accordance with present principles under control of the processor 30.

Now in reference to FIG. 2, a flow chart of example logic to be executed by a processor of a temperature control system in accordance with present principles is shown. Beginning at block 50, the logic receives a predetermined input such as, e.g., a user command that may be a command to begin operation of the temperature control system, to detect a heat exchange catheter line assembly, and/or to begin pumping fluid through at least a portion of the heat exchange catheter line assembly, etc. After receiving the command, the logic moves to decision diamond 52 where the logic determines whether an NFC element such as the NFC element 24 described above is sensed by an NFC member on the temperature control system.

If the logic determines at diamond 52 that an NFC element is sensed in accordance with present principles, the logic then moves to decision diamond 54 where the logic determines whether the signal is indicative of the NFC element being sensed by, e.g., that particular temperature control system or another temperature control system for the first time. Note that in exemplary embodiments, the logic may determine that the NFC element that was sensed may or may not have been sensed by that particular temperature control system or another temperature control system by communicating with a server over the Internet to thereby, e.g., access data on the server or request the server provide an indication as to whether the sensed signal is indicative of the NFC element being sensed for the first time.

Regardless, if the logic determines at diamond 54 that the NFC element has been sensed for the first time by an NFC member, the logic then moves to block 56 where the logic permits normal operation of the temperature control system in accordance with present principles. If, however, the logic determines that the NFC element has been sensed before at diamond 54, the logic instead moves to block 58 where the logic returns "abnormal." More specifically, at block 58 the logic may determine that an abnormal, unauthorized, unapproved, etc. connection of the heat exchange catheter line assembly associated with the NFC element was attempted. For example, an unauthorized attempt may be trying to connect a heat exchange catheter line assembly to the temperature control system where the assembly was manufactured by an entity other than the entity that manufactured the temperature control system. As another example, the unauthorized attempt may be trying to connect a pirated heat exchange catheter line assembly provided by an unauthorized third party to the temperature control system.

Momentarily referring back to decision diamond 52 of FIG. 2, note that if the logic determines that an NFC element has not been sensed, the logic moves from diamond 52 directly to block 58 rather than to diamond 54. The logic may then proceed at block 58 as set forth herein.

Accordingly, from block 58 where the logic returns "abnormal," the logic continues to block 60 where the logic processes "abnormal." For example, the logic may take appropriate action based on the abnormal connection and/or result such as, e.g., generating a warning signal to activate a visual and/or audible warning on the display/speakers of the temperature control system to notify a human operator that an approved heat exchange catheter line assembly is not present and/or cannot be connected. In addition to, or in the alternative, at block 60 the logic may take another action such as, e.g., generating an audio and/or visual warning indicating that the catheter and/or tubing set has been previously used, and/or preventing heat exchange operation of the temperature control system. If the logic prevents heat exchange operation, note that an operator of the temperature control system may be notified of this as well through, e.g., an audio and/or visual notification.

However, it is to be understood that in addition to the foregoing, still other actions may be taken at block 60. As another example, at block 60 the logic may report the use of the heat exchange catheter line assembly for a time other than a first time to the manufacturer of the temperature control system, a healthcare provider, or the proper authorities (e.g., to the manufacturer's server), using, e.g., an Internet connection.

Regardless, it is to be understood that the logic, in determining to return "abnormal" not only when the NFC element that is associated with the heat exchange catheter line assembly is not sensed at all by the NFC member of the temperature control system, but also when the NFC element has been sensed more than once, prevents spoofing of the system through the expedient of holding an authorized NFC element of an authorized heat exchange catheter line assembly close to the temperature control system multiple times to permit multiple uses of non-approved heat exchange catheter line assemblies. To this end, each NFC element may be programmed to provide an encoded secure unique identification to the NFC member, which may simply determine whether that particular ID has been used once already.

Furthermore, to ensure that a single heat exchange catheter line assembly may not be used across multiple temperature control systems, each temperature control system may access a centralized database hosted by the server which lists approved NFC element IDs. When the NFC member of a temperature control system detects an NFC element, it reports the ID of the element to the server, which removes the ID from a data structure of approved NFC elements or otherwise indicates that the ID is no longer approved. In the event that the ID has been reported once already to the server, the server sends a signal to the reporting temperature control system that the reported ID of the NFC element of the heat exchange catheter line assembly sought to be used is not approved, resulting in the temperature control system returning "abnormal."

Now in reference to FIGS. 3-5, screen shots of example user interfaces (UIs) that may be presented on a display of a temperature control system in accordance with present principles are shown. However, it is to be understood that content from each of the screen shots shown in FIGS. 3-5 may be combined or mixed as desired, and that still other content may be presented indicating a status of the system and/or a status of connection to reflect the principles and statuses set forth herein (e.g., "Warning: This assembly is not licensed for use," or "Status: System functioning properly.").

Specifically in reference to FIG. 3, a screen shot 62 includes a warning indicator 64 and an exemplary message 66 indicating that the operator of the temperature control system does not have an authorized component (e.g., a heat exchange catheter line assembly) connected to the temperature control system.

Turning to FIG. 4, a screen shot 68 is shown. The screen shot 68 includes a warning indicator 70 and an exemplary message 72 indicating that the catheter and/or tubing (or another portion of a heat exchange catheter line assembly) has been used already. FIG. 5 shows a screen shot 74 that includes an exemplary message 76 indicating that the component sought to be used with the temperature control system is not an authorized component and/or is a component that has already been used. Note that the message 76 further indicates that the temperature control system is disabled, which may be done in response to a determination by a processor on the temperature control system that the component is not authorized for use and/or has already been used.

Present principles further recognize that, should a temperature control system be disabled, the system may be enabled again in various ways. For example, an administrator at a hospital where the temperature control system is to be employed may have to unlock the system using a physical key (e.g., metallic key), may have to enter an electronic key or passcode to the processor (e.g., using a keypad or other input device on the temperature control system), a service agent associated with the manufacturer of the temperature control system may need to be contacted to receive a passcode or override code to input to the processor, etc. In addition to or in lieu of the above, a monetary fee may be required to receive, e.g., a passcode or override code to unlock or otherwise enable the system for operation again.

Also alternatively or in addition to the above, the system may be permanently disabled upon the first unauthorized use of a component, after one or more components have been attempted for unauthorized use on a particular system a predetermined number of times, or after one or more components have been attempted for unauthorized use a predetermined number of times without an intervening authorized use. Also in the alternative or in addition, the system may be enabled again simply by connecting an authorized component to the system, which may be determined using, e.g., NFC elements and members in accordance with present principles.

Based on the foregoing detailed description, it may now be appreciated that NFC components may be used in accordance with present principles to permit authorized use of various heat exchange components with each other. Furthermore, present principles recognize that NFC components may be associated not just with the heat exchange catheter line assembly as set forth above, but may be associated with still other components for use in conjunction with the assembly and system. Even further, plural NFC elements may be associated with particular portions of the assembly or other components that are detachable and/or otherwise interchangeable.

Present principles also recognize that an NFC member/reader as set forth above may determine that the assembly is approved for use with the temperature control system based on, e.g., information from the NFC element indicating that the assembly is from a licensed assembly provider and/or is from the same provider/manufacturer as the temperature control system.

Additionally, in some implementations particular NFC elements may only permit authorized use of their associated heat exchange catheter line assemblies with particular temperature control systems. In other words, particular NFC elements and NFC members may be associated with each other (e.g., by assigning unique IDs and/or IDs shared only between a particular NFC element and particular NFC member, where the IDs may be security IDs) such that their associated components may be used together and are not interchangeable with other assemblies and systems, even if the other assemblies and systems are from an authorized source.

Further still, in some implementations an NFC member/reader may intermittently sense for and/or communicate with an NFC element already recognized once by the NFC member at the outset of operation of the temperature control system in accordance with present principles in order to continue uninterrupted operation the system. This may be, e.g., for security purposes and/or to ensure that an NFC element has not been removed from its associated assembly or the assembly's proximity for use with another assembly and/or system.

While the particular INTRAVASCULAR HEAT EXCHANGE CATHETER AND SYSTEM WITH RFID COUPLING is herein shown and described in detail, it is to be understood that the subject matter which is encompassed by the present invention is limited only by the claims.

What is claimed is:

1. A system, comprising:
  a heat exchange catheter line assembly configured to convey working fluid circulating to and from at least one heat exchange element on an intravascular heat exchange catheter;
  a heat exchange system configured for fluidly communicating with the heat exchange catheter line assembly to exchange heat with the working fluid, the heat exchange system including at least one processor;
  a near field communication (NFC) member associated with the heat exchange system; and
  an NFC element associated with the heat exchange catheter line assembly, wherein the NFC member is configured to provide the processor with a signal representative of whether the NFC member detects the NFC element, the processor being programmed to disable operation of the system responsive to a determination that a with heat exchange catheter line assembly that is not an assembly authorized for use with the heat exchange system has been attempted for use at least a predetermined number of times greater than one.

2. The system of claim 1, wherein the heat exchange catheter line assembly includes the intravascular heat exchange catheter.

3. The system of claim 1, wherein the heat exchange catheter line assembly includes a tubing set configured to engage the intravascular heat exchange catheter.

4. The system of claim 1, wherein the heat exchange catheter line assembly includes a combination of the intravascular heat exchange catheter and a tubing set configured to engage the intravascular heat exchange catheter.

5. The system of claim 1, comprising a computer memory with instructions executable by the processor to configure the processor at least under one predetermined condition, responsive to a signal from the NFC member that the NFC member does not detect the NFC element, to generate a warning signal to activate a visual warning to a human operator that an approved heat exchange catheter line assembly is not present, or to activate an audible warning, or to activate both a visual and an audible warning.

6. The system of claim 1, comprising a computer memory with instructions executable by the processor to configure the processor at least under one predetermined condition, responsive to a signal from the NFC member that the NFC member does not detect the NFC element, to prevent heat exchange operation of the heat exchange system.

7. The system of claim 1, wherein the NFC member is a radiofrequency identification (RFID) reader and the NFC element is an RFID tag.

8. The system of claim 1, wherein the processor is programmed to maintain disablement of the operation of the system until the processor determines that a valid authorization key is input to the system using a physical key.

9. The system of claim 1, wherein the processor is programmed to maintain disablement of the operation of the system until the processor determines that a valid authorization key is input to the system using an input device receiving input of a passcode representing the valid authorization key.

10. The system of claim 1, wherein the processor is programmed with instructions to disable operation of the system responsive to a determination that a correct NFC element has not been detected by the NFC member.

11. An apparatus, comprising: a heat exchange system
a first heat exchange catheter line assembly configured to convey working fluid circulating to and from at least one heat exchange element on an intravascular heat exchange catheter, the assembly also configured for fluidly communicating with the heat exchange system to exchange heat with the working fluid; and
a near field communication (NFC) element associated with the first heat exchange catheter line assembly and configured to communicate with an NFC member associated with the heat exchange system;
wherein the NFC element is configured to communicate with the NFC member to cause the NFC member to provide a processor on the heat exchange system with a signal indicating that the first heat exchange catheter line assembly is an assembly authorized for use with the heat exchange system, the processor being adapted to establish an operational state of the apparatus selected from one of:
being disabled upon a determination by the processor that a heat exchange catheter line assembly that is not an assembly authorized for use with the heat exchange system has been attempted for use at least a predetermined number of times greater than one;
being disabled upon a determination by the processor that a heat exchange catheter line assembly that is not an assembly authorized for use with the heat exchange system has been attempted for use at least a predetermined number of times without an intervening authorized use.

12. The apparatus of claim 11, wherein the first heat exchange catheter line assembly includes the intravascular heat exchange catheter.

13. The apparatus of claim 11, wherein the first heat exchange catheter line assembly includes a tubing set configured to engage the intravascular heat exchange catheter.

14. The apparatus of claim 11, wherein the first heat exchange catheter line assembly includes a combination of the intravascular heat exchange catheter and a tubing set configured to engage the intravascular heat exchange catheter.

15. The apparatus of claim 11, wherein the NFC element is configured to communicate with the NFC member using radiofrequency identification (RFID).

16. The apparatus of claim 11, wherein the NFC element is configured to communicate with the NFC member to provide a signal to the processor indicating that the first heat exchange catheter line assembly is an assembly authorized for use with that particular heat exchange system and no other heat exchange system.

17. The apparatus of claim 11, wherein the apparatus is enabled after being disabled by connecting an authorized component to the system.

18. The apparatus of claim 11, wherein the state includes being permanently disabled upon determination that the first heat exchange catheter line assembly is not an assembly authorized for use with the heat exchange system.

19. The apparatus of claim 11, wherein the operational state includes being disabled upon a determination that a heat exchange catheter line assembly that is not an assembly authorized for use with the heat exchange system has been attempted for use at least a predetermined number of times greater than one.

20. The apparatus of claim 11, wherein the operational state includes being disabled upon a determination that a heat exchange catheter line assembly that is not an assembly authorized for use with the heat exchange system has been attempted for use at least a predetermined number of times without an intervening authorized use.

\* \* \* \* \*